United States Patent
Banholzer et al.

(10) Patent No.: US 6,881,422 B2
(45) Date of Patent: Apr. 19, 2005

(54) POWDER FORMULATIONS CONTAINING TIOTROPIUM SUITABLE FOR INHALATION

(75) Inventors: Rolf Banholzer, Stuttgart (DE); Manfred Graulich, Waldalgesheim (DE); Christian Kulinna, Attenweiler (DE); Andreas Mathes, Ockenheim (DE); Helmut Meissner, Ingelheim (DE); Peter Seiger, Mittelbiberach (DE); Peter Specht, Ober-Hibersheim (DE); Michael Josef Friedrich Trunk, Ingelheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 22 days.

(21) Appl. No.: 10/406,723

(22) Filed: Apr. 3, 2003

(65) Prior Publication Data

US 2004/0029907 A1 Feb. 12, 2004

(30) Foreign Application Priority Data

Apr. 4, 2002 (EP) ............................................ 02007634

(51) Int. Cl.$^7$ ........................... A61K 9/14; A61K 31/44
(52) U.S. Cl. ...................................... 424/489; 514/291
(58) Field of Search ........................... 424/489; 514/291

(56) References Cited

U.S. PATENT DOCUMENTS

| | | |
|---|---|---|
| 4,042,700 A | 8/1977 | Banholzer et al. |
| 4,608,377 A | 8/1986 | Banholzer et al. |
| 4,783,534 A | 11/1988 | Banholzer et al. |
| 5,610,163 A | 3/1997 | Banholzer et al. |
| 5,654,314 A | 8/1997 | Banholzer et al. |
| 5,770,738 A | 6/1998 | Banholzer et al. |
| 5,952,505 A | 9/1999 | Banholzer et al. |
| 6,486,321 B2 | 11/2002 | Banholzer et al. |
| 6,506,900 B1 | 1/2003 | Banholzer et al. |
| 2002/0110529 A1 * | 8/2002 | Bechtold-Peters et al. .... 424/46 |
| 2003/0043687 A1 | 3/2003 | Boeck et al. |
| 2003/0068278 A1 | 4/2003 | Boeck et al. |
| 2003/0070679 A1 * | 4/2003 | Hochrainer et al. ... 128/203.15 |

FOREIGN PATENT DOCUMENTS

| | | |
|---|---|---|
| WO | WO 99/34778 | 7/1999 |
| WO | WO 00/28979 | 5/2000 |

* cited by examiner

*Primary Examiner*—Raymond J. Henley, III
(74) *Attorney, Agent, or Firm*—Michael P. Morris; Mary-Ellen M. Devlin; Andrea D. Small

(57) ABSTRACT

A method of making a physically stable and homogenous powdered pharmaceutical composition comprising a tiotropium salt and a physiologically acceptable excipient, the method comprising:

(a) suspending the tiotropium salt and the physiologically acceptable excipient in a suspending agent in which the tiotropium salt and the physiologically acceptable excipient are essentially insoluble to obtain a suspension; and (b) removing the suspending agent from the suspension of step (a) to obtain the pharmaceutical composition, the pharmaceutical composition itself, and method of treating respiratory diseases, especially chronic obstructive pulmonary disease and asthma, in a patient in need thereof by administering an effective amount of the pharmaceutical composition to the patient.

14 Claims, No Drawings

POWDER FORMULATIONS CONTAINING TIOTROPIUM SUITABLE FOR INHALATION

FIELD OF THE INVENTION

The invention relates to powdered preparations containing tiotropium for inhalation, processes for preparing them as well as their use for preparing a pharmaceutical composition for treating respiratory complaints, particularly for treating chronic obstructive pulmonary disease (COPD) and asthma.

BACKGROUND OF THE INVENTION

Tiotropium bromide is known from European Patent Application EP 418 716 A1 and has the following chemical structure:

Tiotropium bromide is a highly effective anticholinergic with a long-lasting activity which can be used to treat respiratory complaints, particularly chronic obstructive pulmonary disease (COPD) and asthma. The term tiotropium refers to the free ammonium cation.

For treating the abovementioned complaints, it is useful to administer the active substance by inhalation. In addition to the administration of broncholytically active compounds in the form of metered aerosols and inhalable solutions, the use of inhalable powders containing active substance is of particular importance.

With active substances which have a particularly high efficacy, only small amounts of the active substance are needed per single dose to achieve the desired therapeutic effect. In such cases, the active substance has to be diluted with suitable excipients in order to prepare the inhalable powder. Because of the large amount of excipient, the properties of the inhalable powder are critically influenced by the choice of excipient. When choosing the excipient, its particle size is particularly important. As a rule, the finer the excipient, the poorer its flow properties. However, good flow properties are a prerequisite for highly accurate metering when packing and dividing up the individual doses of preparation, e.g., when producing capsules (inhalettes) for powder inhalation or when the patient is metering the individual dose before using a multi-dose powder inhaler. Moreover, the particle size of the excipient is very important for the emptying characteristics of capsules when used in an inhaler. It has also been found that the particle size of the excipient has a considerable influence on the proportion of active substance in the inhalable powder which is delivered for inhalation. The term inhalable proportion of active substance refers to the particles of the inhalable powder which are conveyed deep into the branches of the lungs when inhaled with a breath. The particle size required for this is between 1 $\mu$m and 10 $\mu$m, preferably less than 6 $\mu$m.

The aim of the invention is to prepare an inhalable powder containing tiotropium which, while being accurately metered (in terms of the amount of active substance and powder mixture released and delivered to the lungs by each inhalation process) with only slight variations between batches, enables the active substance to be administered in a therapeutically effective inhalable proportion.

The fact that tiotropium, particularly tiotropium bromide, has a therapeutic efficacy even at very low doses imposes further conditions on an inhalable powder which is to be used with highly accurate metering. Because only a low concentration of the active substance is needed in the inhalable powder to achieve the therapeutic effect, a high degree of homogeneity of the powder mixture and only slight fluctuations in the dispersion characteristics from one batch to the next are essential. The homogeneity of the powder mixture and minor fluctuations in the dispersion properties are crucial in ensuring that the inhalable proportion of active substance is released reproducibly in constant amounts and with the lowest possible variability.

Accordingly, a further aim of the present invention is to prepare an inhalable powder containing tiotropium which is characterized by a high degree of homogeneity and uniformity of dispersion. The present invention also sets out to provide an inhalable powder which allows the inhalable proportion of active substance to be administered with the lowest possible variability. Furthermore, the present invention sets out to provide an inhalable powder being characterized by a high stability.

DETAILED DESCRIPTION OF THE INVENTION

It was found that, surprisingly, the objective outlined above can be achieved by means of the tiotropium containing powdered preparations for inhalation (inhalable powders) obtainable by the method according to the invention described hereinafter.

Accordingly, the invention relates to a method for preparing a physically stable and homogenous powdered preparation containing tiotropium in admixture with a physiologically acceptable excipient, characterized in that the tiotropium salt and the physiologically acceptable excipient are suspended in a suspending agent, in which the tiotropium salt and the physiologically acceptable excipient are essentially insoluble, and from the thus obtained suspension the suspending agent is removed.

Preferably the invention relates to a method for preparing a physically stable and homogenous powdered preparation containing tiotropium in an amount of 0.001% to 2%.

Preferably the suspending agent applied in the method according to the invention is selected from the group consisting of alkanes, alcohols, ketones, mixtures of alkanes with alcohols, and mixtures of alkanes with ketones. Of particular interest are suspending agents selected from the group consisting of hexane, heptane, methanol, ethanol, and mixtures thereof. Within the scope of the invention, references to hexane or heptane are to be understood as references to all of the possible isomers. However, n-hexane and n-heptane, optionally in admixture with methanol or ethanol, preferably ethanol, are of particular interest. If mixtures of the aforementioned suspending agents are applied, the amount of alkane is preferably at least 90%, more preferably at least 95%. Of particular interest within the scope of the present invention, are mixtures containing at least 98% alkane. In a preferred embodiment the suspending agent is hexane, preferably n-hexane, containing 1%, preferably 0.5% ethanol. In another preferred embodiment the suspending agent is heptane, preferably n-heptane, containing 1%, preferably 0.5% ethanol.

By tiotropium is meant the free ammonium cation. The counter-ion (anion) may be chloride, bromide, iodide, methanesulfonate, p-toluenesulfonate, or methylsulfate. Of these anions, the bromide is preferred. By the term tiotropium salt is meant the salt formed by the cation tiotropium and one of the aforementioned counter-ions (anions). Within the scope of the present invention, tiotropium bromide is preferred of all the tiotropium salts.

References to tiotropium bromide within the scope of the present invention should always be taken as references to all possible amorphous and crystalline modifications of tiotropium bromide. Surprisingly, it has been found that, depending on the reaction conditions and solvent used during the process of preparation of tiotropium bromide, different crystal modifications of tiotropium bromide are obtained. Preferred according to the invention are those powder preparations that contain tiotropium in form of the crystalline tiotropium bromide monohydrate. References to crystalline tiotropium bromide monohydrate within the scope of the present invention should always be taken as references to the crystal modification described in more detail below.

Another object of the invention concerns the tiotropium containing powdered preparations obtainable by the method of preparation according to the invention.

In a preferred embodiment of the invention, the powdered preparations contain 0.001% to 2%, more preferably 0.01% to 1.5% of tiotropium.

The percentages given within the scope of the present invention are always percent by weight if not indicated to the contrary.

Preferably the powdered preparations obtainable according to the invention contain 0.04% to 0.8% tiotropium. Powdered preparations obtainable according to the invention which contain 0.08% to 0.64%, most preferably 0.1% to 0.4% of tiotropium, are particularly preferred according to the invention.

As mentioned hereinbefore, tiotropium bromide is of particular interest within the scope of the present invention. Accordingly, the powdered preparations obtainable according to the invention preferably contain 0.0012% to 2.41%, more preferably 0.012% to 1.81%, of tiotropium bromide. Preferably the powdered preparations obtainable according to the invention contain 0.048% to 0.96% tiotropium bromide. Powdered preparations obtainable according to the invention which contain 0.096% to 0.77%, most preferably 0.12% to 0.48%, of tiotropium bromide, are particularly preferred according to the invention.

Tiotropium bromide is, depending on the choice of reaction conditions and solvents, obtainable in different crystalline modifications. Most preferred according to the invention are those powder preparations, that contain tiotropium in form of the crystalline tiotropium bromide monohydrate. Accordingly, the powdered preparations obtainable according to the invention preferably contain 0.0012% to 2.5%, more preferably 0.0125% to 1.87%, of crystalline tiotropium bromide monohydrate. Preferably the powdered preparations obtainable according to the invention contain 0.05% to 1.0% crystalline tiotropium bromide monohydrate. Powdered preparations obtainable according to the invention which contain 0.1% to 0.8%, most preferably 0.12% to 0.5%, of crystalline tiotropium bromide monohydrate, are particularly preferred according to the invention.

Examples of physiologically acceptable excipients which may be used to prepare the inhalable powders according to the invention include, for example, monosaccharides (e.g., glucose or arabinose), disaccharides (e.g., lactose, saccharose, maltose, or trehalose), oligo- and polysaccharides (e.g., dextrane), polyalcohols (e.g., sorbitol, mannitol, or xylitol), salts (e.g., sodium chloride or calcium carbonate) or mixtures of these excipients with one another. Preferably, mono- or disaccharides are used, while the use of lactose or glucose is preferred, particularly, but not exclusively, in the form of their hydrates. For the purposes of the invention, lactose or glucose are the particularly preferred excipient, while lactose monohydrate and glucose monohydrate are most particularly preferred.

The active substance introduced into the method according to the invention has an average particle size of 0.5 μm to 10 μm, preferably 1 μm to 6 μm, most preferably 1.5 μm to 5 μm. This particle size is obtained by micronization of the tiotropium salt according to methods known in the art.

The inhalable powders according to the invention are preferably characterized in that the excipient has an average particle size of about 20 μm to about 500 μm, more preferably of about 30 μm to about 300 μm, most preferably of about 40 μm to about 200 μm. The phrase average particle size used here denotes the 50% value from the volume distribution measured with a laser diffractometer using the dry dispersion method.

The method according to the invention is described in more detail below.

In a first step tiotropium salt is weight into a mixing vessel. It is apparent for the person skilled in the art that the amount of tiotropium salt added depends on the desired concentration of tiotropium in the final powder formulation. As mentioned hereinbefore, the powdered preparations according to the invention preferably contain 0.001% to 2% tiotropium. In the next step, the suspending agent is added. Preferably such an amount of suspending agent is added that, after addition of all powdered ingredients (active ingredient and excipient), the powder/liquid ratio of the suspension thus obtained is in a range of about 0.1 g/mL to about 2 g/mL, preferably of about 0.2 g/mL to about 1 g/mL, more preferably of about 0.25 g/mL to about 0.85 g/mL. In a further preferred embodiment, the amount of suspending agent leads to a powder/liquid ration of about 0.4 g/mL to about 0.75 g/mL. According to one embodiment of the invention, the total amount of the suspending agent can be directly added. In a yet preferred embodiment according to the invention, the suspending agent is added in at least two, preferably two portions, the first portion being added to the tiotropium salt, the second portion being added after addition of the excipient. If the suspending agent is added in two portions, the first portion added is about 10% to 90%, preferably 20% to 70%, more preferably 30% to 60%, of the suspending agent used in total. After addition of the suspending agent, the suspension thus obtained is stirred and optionally subjected to sonic treatment for about 1 minute to 60 minutes, preferably 2 minutes to 30 minutes. However, it is apparent for the person skilled in the art that the mixing and optionally sonic treatment time may vary from the time periods mentioned hereinbefore in dependence on the batch size of the prepared inhalation powder. After mixing and optionally sonic treatment, the physiologically acceptable excipient is added. If according to a preferred embodiment of the invention, only one portion of the suspending agent has been added in the process steps described hereinbefore, the remaining suspending agent is added after addition of the excipient. After addition of the suspending agent, the suspension thus obtained is stirred and optionally subjected to sonic treatment for about 1 minute to 60 minutes, preferably 2 minutes to 30 minutes. However, it is apparent for the person skilled in the art that the mixing and optionally sonic treatment time may vary from the time periods mentioned hereinbefore in dependence on the batch size of the prepared inhalation powder. Thereafter, the suspending agent is removed by means of filtration, centrifugation and/or evaporation, preferably by filtration or centrifugation. The residue thus obtained is dried at reduced pressure (preferably less than 300 mbar, more preferably between 20 mbar to 200 mbar, most preferred between 30 mbar to 100 mbar) for about 0.5 hour to about 12 hours, preferably for about 1 hour to about 6 hours, more preferably for about 1.5 hours to about 4 hours, either at room temperature or at elevated temperature (preferably more than 20° C., more preferably between 20° C. to 60° C., most preferred between 25° C. to 50° C.). During the period of drying the powder is optionally turned around several times (for instance, every 30 minutes to 60 minutes). After drying, the powder may optionally be sieved. Before filling into the appropriate device or storage chamber or the like, the resulting powder may optionally be exposed to certain environmental conditions (i.e., temperature: 10° C. to 60° C., preferably 20° C. to 45° C.; humidity 20% to 85% r.h., preferably 35% to 75% r.h.) for about 6 hours to about 3 to 4 days, preferably for about 10 hours to 72 hours, more preferably for about 12 hours to 60 hours.

One object of the invention concerns the tiotropium containing powdered preparations obtainable by the method of preparation described hereinbefore.

Another object of the invention concerns the use of the tiotropium containing powdered preparations according to the invention for the manufacture of a medicament suitable for inhalation. Another embodiment of the invention concerns the use of the tiotropium containing powdered preparations according to the invention for the manufacture of a medicament for the treatment of respiratory diseases, in particular asthma or chronic obstructive pulmonary disease (COPD).

The inhalable powders according to the invention may, for example, be administered using inhalers which meter a single dose from a reservoir by means of a measuring chamber (e.g., according to U.S. Pat. No. 4,570,630) or by other means (e.g., according to DE 36 25 685 A).

The following Examples serve to illustrate the present invention further without restricting its scope to the embodiments provided hereinafter by way of example.

Starting Materials

In the Examples which follow, lactose-monohydrate (110M) is used as the excipient. The lactose-monohydrate used was obtained from Messrs DMV International, 5460 Veghel/NL (Product name Pharmatose 110M).

Preparation of Tiotropium Bromide Monohydrate 15.0 kg of tiotropium bromide as obtainable according to the methods disclosed in EP 418 716 A1 are added to 25.7 kg of water In a suitable reaction vessel. The mixture is heated to 80° C. to 90° C. and stirred at constant temperature until a clear solution is formed. Activated charcoal (0.8 kg) moistened with water, is suspended in 4.4 kg of water and this mixture is added to the solution containing the tiotropium bromide and rinsed with 4.3 kg of water. The mixture thus obtained is stirred for at least 15 minutes at 80° C. to 90° C. and then filtered through a heated filter into an apparatus which has been preheated to an outer temperature of 70° C. The filter is rinsed with 8.6 kg of water. The contents of the apparatus are cooled at 3° C. to 5° C. every 20 minutes to a temperature of 20° C. to 25° C. The apparatus is further cooled to 10° C. to 15° C. using cold water and crystallization is completed by stirring for at least one hour. The crystals are isolated using a suction drier, the crystal slurry isolated is washed with 9 liters of cold water (10° C. to 15° C.) and cold acetone (10° C. to 15° C.). The crystals obtained are dried in a nitrogen current at 25° C. over 2 hours. Yield: 13.4 kg of tiotropium bromide monohydrate (86% of theory)

The crystalline tiotropium bromide monohydrate obtainable using the method described above was investigated by DSC (Differential Scanning Calorimetry). The DSC diagram shows two characteristic signals. The first, relatively broad, endothermic signal between 50° C. to 120° C. can be attributed to the dehydration of the tiotropium bromide monohydrate into the anhydrous form. The second, relatively sharp, endothermic peak at 230° C.±5° C. can be ascribed to the melting of the substance. This data was obtained using a Mettler DSC 821 and evaluated using the Mettler STAR software package. The data was recorded at a heating rate of 10 K/min.

The crystalline tiotropium bromide monohydrate obtainable using the method described above was characterized by IR spectroscopy. The data was obtained using a Nicolet FTIR spectrometer and evaluated with the Nicolet OMNIC software package, version 3.1. The measurement was carried out with 2.5 µmol of tiotropium bromide monohydrate in 300 mg of KBr.

Measuring equipment: Laser diffraction spectrometer (HELOS), Sympatec
Dispersing unit: RODOS dry disperser with suction funnel, Sympatec
Sample quantity: 50 mg to 400 mg
Product feed: Vibri Vibrating channel, Messrs. Sympatec
Frequency of vibrating channel: 40% rising to 100%
Duration of sample feed: 15 s to 25 s (in the case of 200 mg)
Focal length: 100 mm (measuring range: 0.9 µm to 175 µm)
Measuring time: about 15 s (in the case of 200 mg)
Cycle time: 20 ms
Start/stop at: 1% on channel 28
Dispersing gas: compressed air
Pressure: 3 bar
Vacuum: maximum
Evaluation method: HRLD Sample Preparation/Product Feed About 200 mg of the test substance are weighed onto a piece of card. Using another piece of card, all the larger lumps are broken up. The powder is then sprinkled finely over the front half of the vibrating channel (starting about 1 cm from the front edge). After the start of the measurement, the frequency of the vibrating channel is varied from about 40% up to 100% (towards the end of the measurement). The sample should be fed in as continuously as possible; however, the amount of product should not be so great that adequate dispersion cannot be achieved. The time over which the entire sample is fed in is about 15 to 25 seconds for 200 mg, for example.

B. Determining the Particle Size of the Excipient

Measuring Equipment and Settings

The equipment is operated according to the manufacturer's instructions.

The following table shows some of the essential bands of the IR spectrum.

| Wave number (cm⁻¹) | Attribution | Type of oscillation |
| --- | --- | --- |
| 3570, 410 | O—H | elongated oscillation |
| 3105 | Aryl C—H | elongated oscillation |
| 1730 | C=O | elongated oscillation |
| 1260 | Epoxide C—O | elongated oscillation |
| 1035 | Ester C—OC | elongated oscillation |
| 720 | Thiophene | cyclic oscillation |

The crystalline tiotropium bromide monohydrate obtainable using the method described above was characterized by X-ray structural analysis. The measurements of X-ray diffraction intensity were carried out on an AFC7R-4-circuit diffractometer (Rigaku) using monochromatic copper $K_\alpha$ radiation. The structural solution and refinement of the crystal structure were obtained by direct methods (SHELXS86 Program) and FMLQ-refinement (TeXsan Program). The X-ray structural analysis carried out showed that crystalline tiotropium bromide monohydrate has a simple monoclinic cell with the following dimensions: a=18.0774 Å, b=11.9711 Å, c=9.9321 Å, β=102.691°, V=2096.96 Å³.

The crystalline tiotropium bromide monohydrate obtainable using the method described above is micronized by known methods, to bring the active substance into the average particle size which meets the specifications according to the invention.

The method of determining the average particle size of the various ingredients of the formulation according to the invention is described as follows.

A. Determining the Particle Size of Micronised Tiotropium Bromide Monohydrate

Measuring Equipment and Settings

The equipment is operated according to the manufacturer's instructions.

Measuring equipment: Laser diffraction spectrometer (HELOS), Sympatec
Dispersing unit: RODOS dry disperser with suction funnel, Sympatec
Sample quantity: 500 mg
Product feed: VIBRI Vibrating channel, Messrs. Sympatec
Frequency of vibrating channel: 18% rising to 100%
Focal length (1): 200 mm (measuring range: 1.8 µm to 350 µm)
Focal length (2): 500 mm (measuring range: 4.5 µm to 875 µm)
Measuring time: 10 s
Cycle time: 10 ms
Start/stop at: 1% on channel 19
Pressure: 3 bar
Vacuum: maximum
Evaluation method: HRLD Sample Preparation/Product Feed About 500 mg of the test substance are weighed onto a piece of card. Using another piece of card, all the larger lumps are broken up. The powder is then transferred into the funnel of the vibrating channel. A gap of 1.2 mm to 1.4 mm is set between the vibrating channel and funnel. After the start of the measurement, the amplitude setting of the vibrating channel is increased from 0% to 40% until a continuous flow of product is obtained, then it is reduced to an amplitude of about 18%. Towards the end of the measurement, the amplitude is increased to 100%.

EXAMPLE 1

Crystalline tiotropium bromide monohydrate is weight into a mixing vessel (0.85 g). 400 mL of the suspending agent (n-hexane+0.5% ethanol) is added. The suspension is mixed (i.e., by means of a paddle mixer; mixing speed 200 rpm) and sonicated for 5 minutes. Mixing is continued without sonification for 5 minutes. 550 g Pharmatose 110M and 800 mL of the suspending agent (n-hexane+0.5% ethanol) is added and mixing is continued for 5 minutes (mixing speed 450 rpm). After mixing is completed, the suspending agent is removed by means of filtration. The residue after filtration is dried in a vacuum (50 mbar to 60 mbar) for 2 hours at 30° C. After drying, the powder is sieved by means of a 0.5 mm sieve. The resulting powder is exposed to certain environmental conditions (temperature 21° C., 60% to 70% r.h), for 1 to 2 days before it is filled into the device.

EXAMPLE 2

Experiment conducted as described in Example 1 with 1.7 g of crystalline tiotropium bromide monohydrate.

EXAMPLE 3

Crystalline tiotropium bromide monohydrate is weight into a mixing vessel (1.7 g). 400 mL of the suspending agent (n-hexane+0.5% ethanol) is added. The suspension is mixed (i.e., by means of a paddle mixer; mixing speed 200 rpm) and sonicated for 5 minutes. Mixing is continued without sonification for 5 minutes. 550 g Pharmatose 110M and 400 mL of the suspending agent (n-hexane+0.5% ethanol) is added and the suspension thus obtained is mixed for 5 minutes (mixing speed 450 rpm) and sonicated. After mixing is completed, the suspending agent is removed by means of filtration. The residue after filtration is dried in a vacuum (50 mbar to 60 mbar) for 2 hours at 25° C. The resulting powder is exposed to certain environmental conditions (temperature 21° C., 60% to 70% r.h), for 1 to 2 days before it is filled into the device.

We claim:

1. A method of making a physically stable and homogenous powdered pharmaceutical composition comprising a tiotropium salt and a physiologically acceptable excipient, the method comprising:
   (a) suspending the tiotropium salt and the physiologically acceptable excipient in a suspending agent in which the tiotropium salt and the physiologically acceptable excipient are essentially insoluble to obtain a suspension; and
   (b) removing the suspending agent from the suspension of step (a) to obtain the pharmaceutical composition.

2. The method of claim 1, wherein the tiotropium salt and the physiologically acceptable excipient are added to the suspending agent separately.

3. The method of claim 2, wherein the tiotropium salt is added to the suspending agent before the physiologically acceptable excipient.

4. The method of claim 2, wherein the physiologically acceptable excipient is added to the suspending agent before the tiotropium salt.

5. The method of claim 1, wherein the tiotropium salt and the physiologically acceptable excipient are added to the suspending agent together.

6. The method according to claim 1, wherein the pharmaceutical composition contains tiotropium in an amount of 0.001% to 2% of the composition.

7. The method according to claim 1, wherein the suspending agent is selected from the group consisting of: alkanes, alcohols, ketones, mixtures of alkanes with alcohols, and mixtures of alkanes with ketones.

8. The method according to claim 6, wherein the suspending agent is selected from the group consisting of: alkanes, alcohols, ketones, mixtures of alkanes with alcohols, and mixtures of alkanes with ketones.

9. The method according to claim 1, wherein the powder/liquid ratio of the suspension is in a range of about 0.1 g/mL to about 2 g/mL.

10. The method according to claim 6, wherein the powder/liquid ratio of the suspension is in a range of about 0.1 g/mL to about 2 g/mL.

11. A method of making a physically stable and homogenous powdered pharmaceutical composition comprising a tiotropium salt and a physiologically acceptable excipient, the method comprising:

(a) adding a first portion of suspending agent to tiotropium salt to obtain a suspension;

(b) mixing and optionally sonically treating of the suspension of step (a);

(c) adding a physiologically acceptable excipient to the suspension of step (b);

(d) adding another portion of suspending agent to the suspension of step (c);

(e) mixing and optionally sonically treating the suspension of step (d);

(f) removing the suspending agent from the suspension of step (e) to obtain a residue; and (g) drying the residue to obtain the pharmaceutical composition.

12. The method according to claim 11, wherein the pharmaceutical composition contains tiotropium in an amount of 0.001% to 2% of the composition.

13. The method according to claim 11, wherein the suspending agent is selected from the group consisting of: alkanes, alcohols, ketones, mixtures of alkanes with alcohols, and mixtures of alkanes with ketones.

14. The method according to claim 11, wherein the powder/liquid ratio of the suspension of step (e) is in a range of about 0.1 g/mL to about 2 g/mL.

* * * * *